United States Patent [19]
Kim

[11] Patent Number: 5,885,072
[45] Date of Patent: Mar. 23, 1999

[54] AUTOMATIC LIGATION TOOL TO FASTEN LIGATURE WIRE TO ORTHODONTIC BRACKET USING DRIVING APPARATUS

[76] Inventor: Joong H. Kim, 1691-8, Seocho 1-Dong, Seoul, Rep. of Korea

[21] Appl. No.: 864,864

[22] Filed: Oct. 23, 1996

[30] Foreign Application Priority Data

Oct. 23, 1995 [KR] Rep. of Korea .................. 1995-36685

[51] Int. Cl.$^6$ ..................................................... A61C 7/00
[52] U.S. Cl. ............................................... 433/3; 600/139
[58] Field of Search ............................ 433/3, 4, 15, 114; 606/144, 139

[56] References Cited

U.S. PATENT DOCUMENTS

| | | | |
|---|---|---|---|
| 2,532,200 | 11/1950 | Smith | 433/3 |
| 3,596,357 | 8/1971 | Matsumoto | 433/3 |
| 3,759,302 | 9/1973 | Attemborough | 433/3 |
| 3,861,045 | 1/1975 | Canter et al. | 433/3 |
| 4,392,494 | 7/1983 | Ashby | 433/4 |
| 4,875,855 | 10/1989 | Beckett | 433/3 |
| 5,125,830 | 6/1992 | Reinhard et al. | 433/3 |
| 5,542,843 | 8/1996 | Price | 433/4 |

*Primary Examiner*—Ralph A. Lewis
*Attorney, Agent, or Firm*—Oliff & Berridge, PLC

[57] ABSTRACT

The invention provides an automatic ligation tool which comfortably and quickly fastens ligature wires to brackets. There is provided an automatic ligation tool for orthodontists for fastening ligature wires to a bracket, that includes a tube with a first end portion having a side provided with first and second openings, a second end portion having an outer surface and an external screw thread on the outer surface, and an inner surface provided with a protuberance; a body including an inner surface provided with an internal screw thread associated with the external thread of the tube, guide grooves formed along the longitudinal direction on the inner surface of the body and a circumscribed groove formed between the internal screw thread and the guide grooves on the inner surface of the body; a rotation shaft inserted into the tube and the body, the shaft having first and second end parts, the first end part formed as a hook which extends out of the first opening, the first end part having an end extending into the second opening, the shaft having guide pins fitting in and sliding along the guide grooves; an elastic device positioned between the protuberance and the guide pins for providing a return force for the shaft; and a driving mechanism connected with the second and part of the shaft for rotating the shaft to fasten the ligature wire gripped by the hook to the bracket.

5 Claims, 5 Drawing Sheets

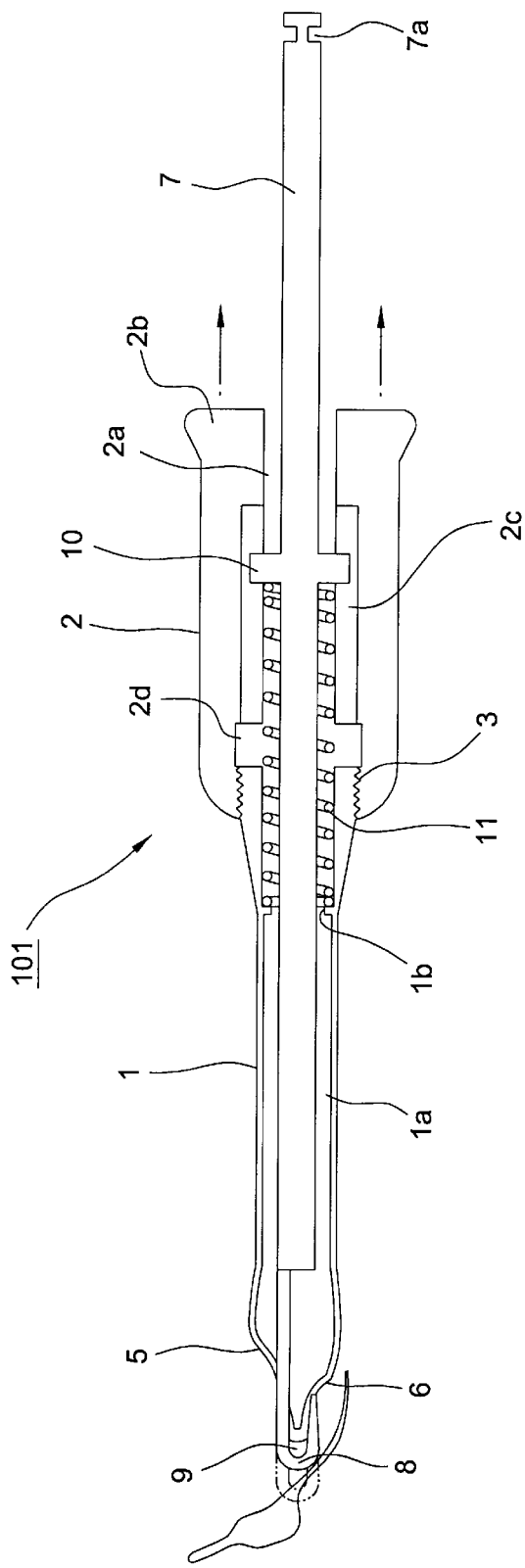
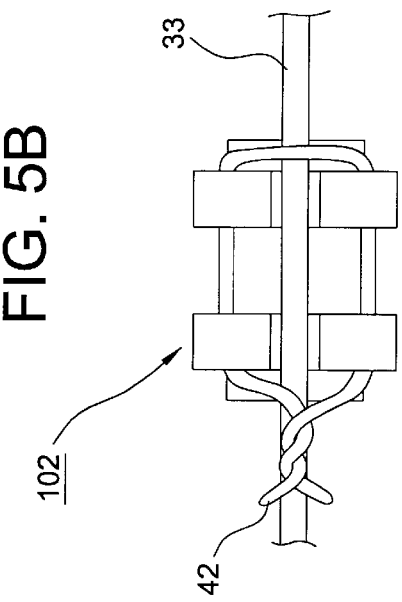
FIG. 5A
FIG. 5B

5,885,072

AUTOMATIC LIGATION TOOL TO FASTEN LIGATURE WIRE TO ORTHODONTIC BRACKET USING DRIVING APPARATUS

BACKGROUND OF THE INVENTION

1. Field of Invention

The present invention relates to an automatic ligation tool, and more specifically, to an automatic ligation tool capable of fastening ligature wire to an orthodontic bracket using a driving apparatus.

2. Description of Related Art

One of the important functions of orthodontics is to correct irregular arrangements of teeth in the dental arch. The is conventional technique for correcting such irregular arrangements of teeth includes the use of mounting a metal arch wire with a bracket an each tooth. Corrective forces are then imparted to selected teeth by means of ligature wires, springs and tensioning devices including elastic ligatures in the form at elastic O-rings and the like.

Generally, as can be seen in FIG. 1, an orthodontic bracket is composed of a base 31, a slot 32a, an identification mark 34, and a stem 32 having tie wing 32b. The base 31 is slightly larger than the center section of the bracket 102 and is concave to conform to the surface of the patient's tooth. The slot 32a is slightly angled to the horizontal center line of the bracket 102 to receive an arch wire 33 which makes an ideal dentition. The tie wing 32b is of rhomboidal construction and is used for securing and coming in contact with a ligature wire 35. The identification mark allows an orthodontist quicker identification when rebinding a loose bracket. The ligature wire 35 holds the arch wire 33 which makes an ideal dentition after the bracket 102 is set to the patient's teeth. The stem is an integral part of the base 31, which receives the ligature wire 35 or an elastic ligature.

As more clearly shown FIG. 2B a ligature wire 42, to be fastened to the bracket 102, has an elongated portion to receive and fix the arch wire, and a rectangular or oblong portion to receive the bracket. In fastening the ligature wire 42 to the bracket 102 to impart corrective forces, the steps for operating the ligature wire 42 are as follows: the first step is to grasp the end portion of the ligature wire 42 and to mount the rectangular portion on the stem formed between the tie wings 32a and the base 31; and the second step is to stretch the ligature wire 42 and rotate the end portion about 10 to 13 times. Therefore, in order to fasten such ligature wires to the bracket, an orthodontic ligature plier 41 known in the prior art has been used, as shown in FIG. 2A.

However, the prior art system for fastening the ligature wire by means of the aforementioned ligature plier has problems in that the operator easily fatigues when he fastens a lot of ligature wires to the brackets, and it takes the operator a lot of time to rotate each ligature wire by using the ligature plier. To overcome these disadvantages of the prior art of fastening the ligature wire to the bracket by means of the ligature plier, the dentist attaches the elastic ligature 43 onto the stem of the bracket, as shown in FIG. 2C. The elastic ligature 43 fastens the bracket 102 to the arch wire 33. The elastic ligature 43 having a high friction coefficient, however, hinders the bracket 102 from moving along the arch wire 33. Also, the elastic ligature 41 will change its color in an oral cavity and decrease its elasticity with the absorption of moisture.

The present invention provides an automatic ligation tool which overcomes the above mentioned problems of the prior art system for attaching the bracket. The automatic ligation tool according to the present invention allows the dentist to comfortably and quickly fasten the ligature wire to the bracket, and will serve well in the orthodontic field.

SUMMARY OF THE INVENTION

An object of the present invention in to provide an automatic ligation tool which overcomes the aforementioned disadvantages of the prior art for fastening ligature wires to brackets.

Another object of the present invention is to provide a novel automatic ligation tool for simply and efficiently fastening ligature wires.

To achieve the above purpose, there is provided an automatic ligation tool for orthodontists for fastening ligature wires to a bracket, comprising: a tube including a first end portion having a side provided with first and second openings, a second end portion having an outer surface and an external screw thread on the outer surface, and an inner surface provided with a protuberance; a body including an inner surface provided with an internal screw thread associated with the external thread of the tube, guide grooves formed along the longitudinal direction on the inner surface of the body and a circumscribed groove formed between the internal screw thread and the guide grooves on the inner surface of the body; a rotation shaft inserted into the tube and the body, the shaft having first and second end parts, the first end part formed as a hook which extends out of the first opening, the first end part having an end extending into the second opening, the shaft having guide pins fitting in and sliding along the guide grooves; an elastic means positioned between the protuberance and the guide pins for providing a return force for the shaft; and a driving means connected with the second end part of the shaft for rotating the shaft to fasten the ligature wire gripped by the hook to the bracket.

BRIEF DESCRIPTION OF THE DRAWINGS

Other objects and aspects of the invention will become apparent from the following description of embodiments with reference to the accompanying drawings, in which:

FIGS. 5A and 5B are views illustrating the operation of the tool illustrated in FIG. 3.

DETAILED DESCRIPTION OF PREFERRED EMBODIMENTS

The above object and advantages of the present invention will become more apparent from the detailed description of the preferred embodiment below and by referring to the attached drawings.

Figure 1:
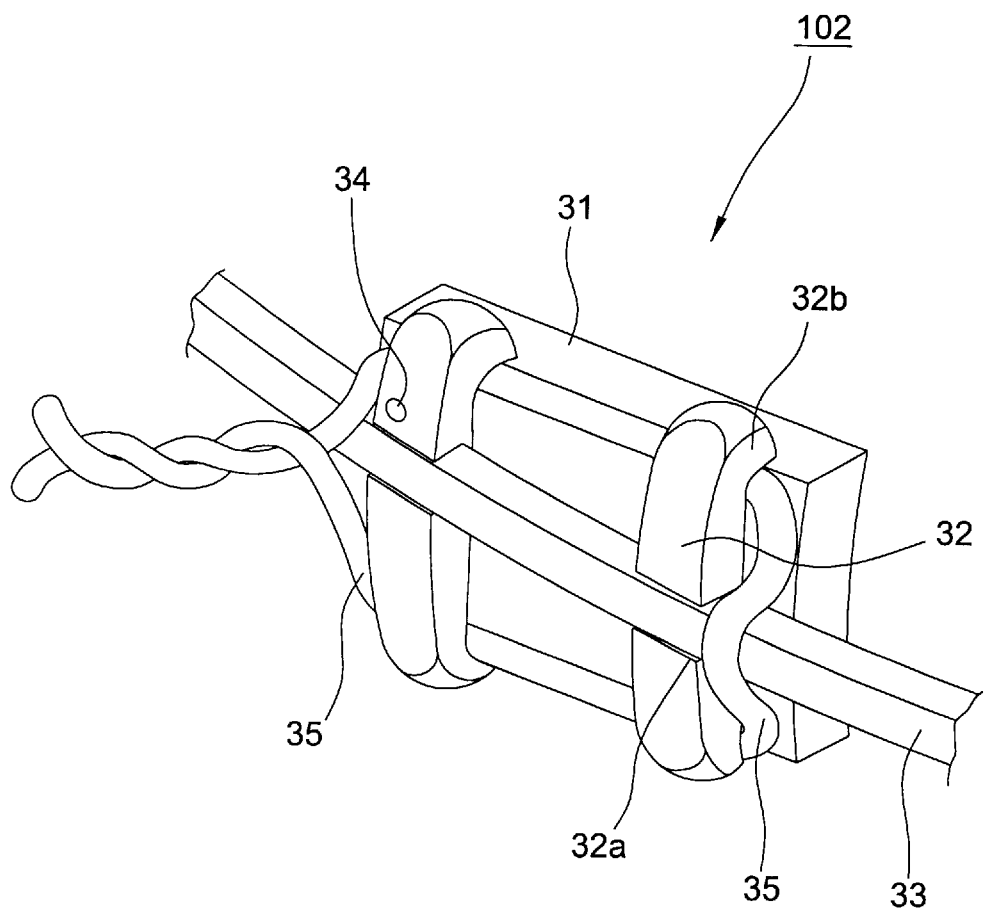
FIG. 1 is a perspective view of a bracket associated with a ligature wire and an arch wire.
Figure 2A:
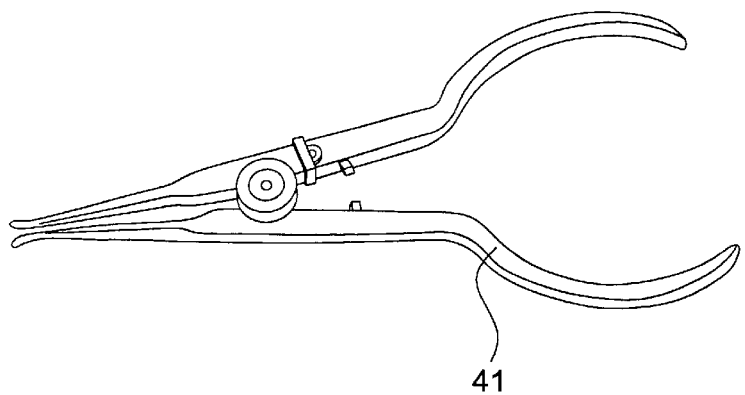
FIG. 2A is a perspective view of an orthodontic ligature plier.
Figure 2B:
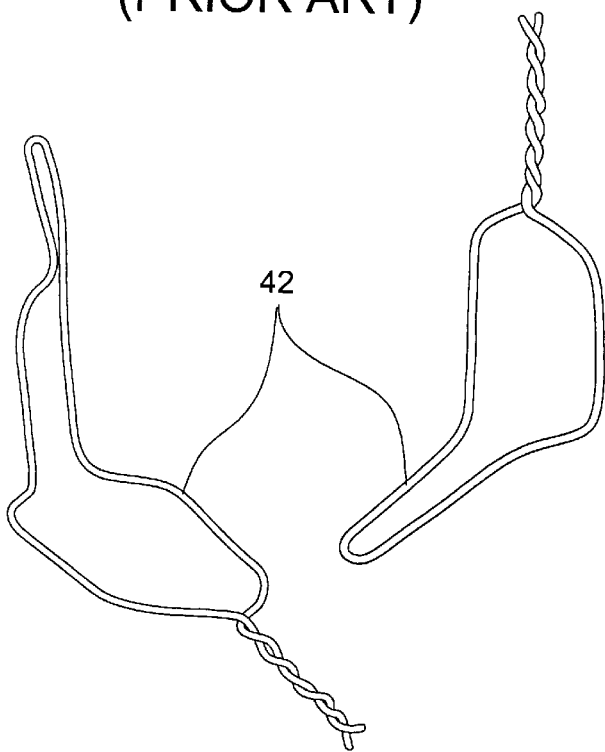
FIG. 2B is perspective view of a ligature wire.
Figure 2C:
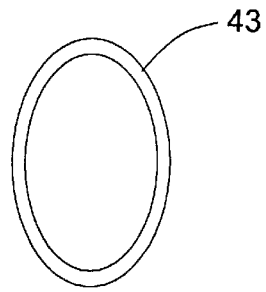
FIG. 2C is perspective view of an elastic ligature.
Figure 3:
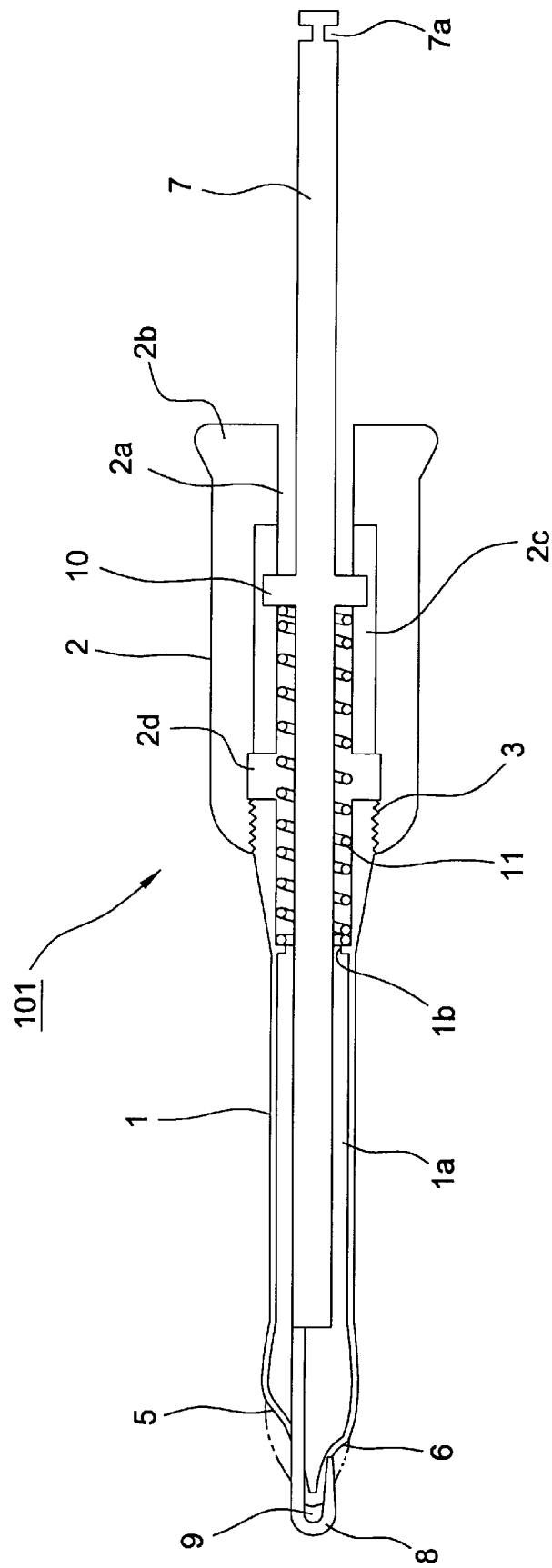
FIG. 3 is a sectional view and partially exploded view of an automatic ligation tool according to the present invention.
Figure 4A:
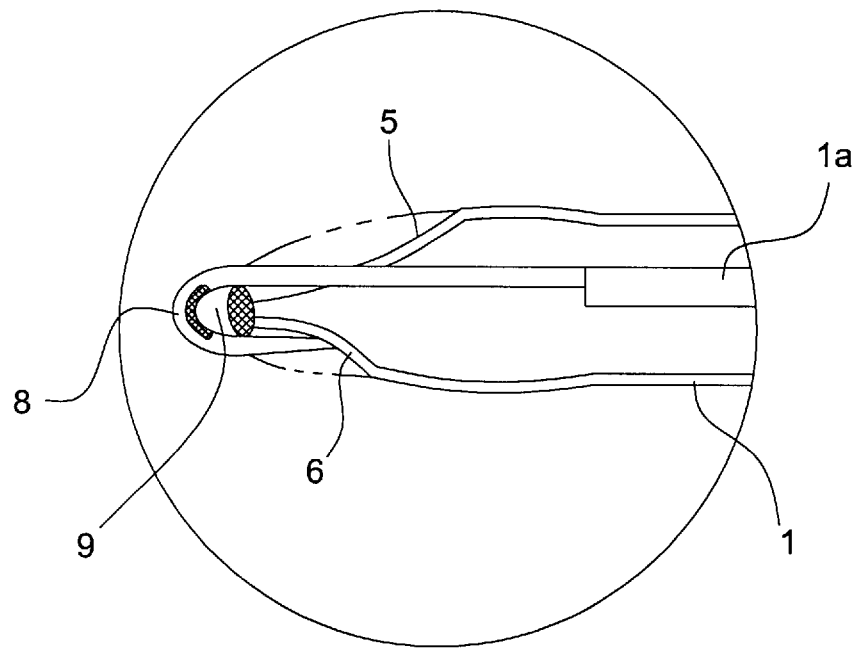
FIG. 4A is a partial cross-sectional view of an automatic ligation tool according to the present invention.
Figure 4B:
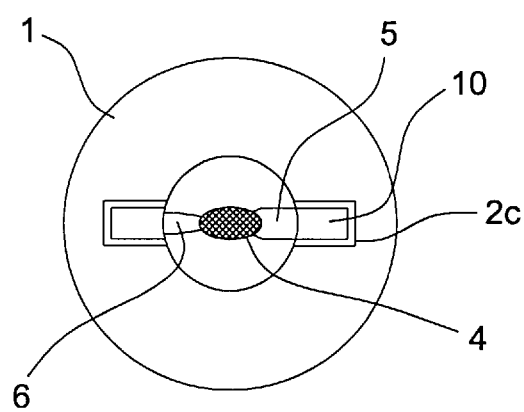
FIG. 4B is a front view of an automatic ligation tool of FIG. 3.

As shown in FIG. 3, an automatic ligation tool includes a tube 1, a body 2 and a rotation shaft 7 which is inserted through the tube 1 and the body 2. The tube 1 includes two end portions. One end portion of the tube 1 being of domed configuration, which provides space where the rotation shaft 7 easily gets there and back, has two openings 5 and 6 which are formed on both sides of dome ended portion. As more clearly shown in FIGS. 4A and 4B, the end portion of the tube 1 has a blunt end 4 of which the surface is rasped so that the ligature wire can be firmly gripped. The other end portion of the tube 1, having an external screw thread on its outer surface, is associated with the body 2. A circumscribed protuberance 1*b* is formed on the inner surface of the tube 1.

The body 2 includes an internal screw thread which is associated with the external screw thread of the tube 1, a circumscribed groove 2*d* and guides grooves 2*c* on its inner surface. The internal screw thread and the external screw thread are formed as a right-handed screw in case the shaft 7 is rotated in the clockwise direction or a left-handed screw in case the shaft 7 is rotated in the counterclockwise direction so that the tube 1 can be firmly connected with the body 2.

The circumscribed groove 2*d* is formed between the internal screw thread and the guide grooves 2*c*. The circumscribed groove 2*d* is deeper than the guide groove 2*c* and enables the rotation shaft 7 to be easily separated from the tube 1 and the body 2. The guide grooves 2*c* are formed along the longitudinal direction of the body 2 so that the rotation shaft 7 can slide back and forth.

The rotation shaft 7, which is inserted into the tube 1 and the body 2, has two and parts and two guide pins 10. One end part of the shaft 7 being of U-shaped configuration is formed as a hook 8 which extends out of the first opening 5 into the second opening 6. The inward surface of the hook 8 is rasped to assure that the ligature wire 42 can be firmly gripped between the blunt end 4 and the hook 8. The two guide pins 10 fit in and slide along the guide grooves 2*c* when the rotation shaft 7 is pulled and set back. Thus, as the rotation shaft 7 rotates, the two guide pins 10 fitted in the guide groove 2*c* rotate the tube 1 and the body 2. Accordingly, the ligature wire 42 gripped between the blunt end 4 and the hook 8 is wound by the rotation of the rotation shaft 7. The connection groove 7*a* formed in the rotation shaft 7 is connected with an apparatus (not shown) for driving the automatic ligation tool.

A spring 11 is positioned between the circumscribed protuberance 1*b* and the guide pins 10 so that the body 2 associated with the tube 1 can be restored to the original position by the elastic force of the spring 11 which allows the hook 8 to grip the ligature wire 42 in cooperation with the blunt end 4.

A driving apparatus, such as an orthodontic hand-piece motor known in the field of orthodontic dentistry like a rechargeable drive motor or a stepping motor and so forth, will provide the switch modes which permit the operator to adjust the rotative speed.

Also, a computer, including control circuits connected to the switch modes, generates a control signal to control the rotative speed and the number of revolutions per minutes of the driving apparatus. This type of computer including such control circuits can be easily made by a person skilled in the prior art.

Referring to FIGS. 5A and 5B, the steps for ligating the ligature wire to the bracket are as follows: first, the operator pulls back the body 2 to move the rotation shaft 7 forward, inserts the end portion of the ligature wire 42 between the blunt end 4 of the tube 1 and the hook 8 and mounts the rectangular portion of the ligature wire 42 onto the stem formed between the tie wings and the base; second, then the rotation shaft 7 is restored to the original position and the ligature wire 42 is firmly gripped between the blunt end 4 of the tube 1 and the hook 8 by the elastic force of the spring 11; and third, then the operator switches on the driving apparatus or the computer connected with the driving apparatus. The automatic ligation tool is rotated at a predetermined speed or revolutions per minutes (R.P.M.) so that the ligature wire may be fastened to the bracket.

On the other hand, in order to disassemble the automatic ligation tool, the operator separates the tube 1 from the body 2, pulling back the body 2 until the guide pins 10 of the rotation shaft 7 are inserted into the guide groove 2*d*. Thereafter, the operator can separate the spring 11 and the rotation shaft 7 from the body 2 in one continuous motion.

As is apparent from the above discussion, the present invention provides the ligature wire with a firm fastening through a simple structure, thus reducing the working time. Also, the present invention increases the reliability of the ligature wire fastened to the bracket, and is easy to maintain, assemble and disassemble the ligation tool for orthodontic dentistry.

It is to be understood that the above description is limited to a preferred embodiment of this invention, and should not be read to limit the invention in any manner.

I claim:

1. An automatic ligation tool for orthodontists for fastening ligature wires to a bracket, comprising:

a tube including a first end portion having a side provided with first and second openings and a second end portion having an external thread, said tube further including an internal protuberance between said first and second end portions;

a body including an inner surface provided with an internal screw thread associated with the external thread of the tube, guide grooves formed along a longitudinal direction on the inner surface of the body and a circumscribed groove formed between the internal screw thread and the guide grooves on the inner surface of the body;

a rotation shaft inserted into the tube and the body, the shaft having first and second end parts, the first end part formed as hook which extends out of the first opening, the first end part having an end extending into the second opening, the shaft having guide pins fitting in and sliding along the guide grooves;

elastic means positioned between the protuberance and the guide pins for providing a return force for the shaft; and a driving means connected with the second end part of the shaft for rotating the shaft to fasten the ligature wire gripped by the hook to the bracket.

2. The automated ligation tool according to claim 1, wherein the first end portion of the tube has a blunt end provided with a surface that is rasped.

3. The automatic ligation tool according to claim 1, wherein the hook is provided with an inward surface which is rasped.

4. The automatic ligation tool according to claim 1, wherein the internal screw thread and the external screw thread are formed as right-handed screws when the shaft is designed to be rotated in the clockwise direction.

5. The automatic ligation tool according to claim 1, wherein the internal screw thread and the external screw thread are formed as left-handed screws when the shaft is designed to be rotated in the counterclockwise direction.

* * * * *